(12) United States Patent
Smith

(10) Patent No.: US 6,414,310 B1
(45) Date of Patent: Jul. 2, 2002

(54) AUTOMATIC CONTROL CIRCUIT FOR INFRARED DETECTORS

(75) Inventor: Patrick George Smith, Shakopee, MN (US)

(73) Assignee: Sensor Electronics Corporation, Minneapolis, MN (US)

( * ) Notice: Subject to any disclaimer, the term of this patent is extended or adjusted under 35 U.S.C. 154(b) by 0 days.

(21) Appl. No.: 09/431,975

(22) Filed: Oct. 29, 1999

(51) Int. Cl.⁷ .................................................. G01J 5/00

(52) U.S. Cl. .................................................. 250/338.1

(58) Field of Search ................................. 250/366, 349, 250/338.1

(56) References Cited

U.S. PATENT DOCUMENTS

| | | | | |
|---|---|---|---|---|
| 4,153,837 A | * | 5/1979 | Ross | 250/343 |
| 5,184,017 A | * | 2/1993 | Tury et al. | 250/343 |
| 5,332,901 A | * | 7/1994 | Eckles et al. | 250/345 |
| 6,201,245 B1 | * | 3/2001 | Schrader | 250/349 |

* cited by examiner

*Primary Examiner*—Georgia Epps
*Assistant Examiner*—M. Hasan
(74) *Attorney, Agent, or Firm*—Paul L. Sjoquist

(57) ABSTRACT

A circuit for measuring the relative absorption signals from an infrared detector to measure gas concentrations in the detector, wherein an absorption gas wavelength signal is compared to a reference gas wavelength signal, through circuits and a computer processor, together having automatic compensation for absorption variables and which permit the measurement of gas absorption by use of Beer's Law equations.

12 Claims, 3 Drawing Sheets

AUTOMATIC CONTROL CIRCUIT FOR INFRARED DETECTORS

BACKGROUND OF THE INVENTION

The present invention relates to infrared detectors used primarily for detecting gas concentrations in a confined space, usually defined as a fixed distance of space between an infrared source and an infrared detector. More particularly, the invention relates to electronic control circuits for receiving analog electrical signals from such infrared detectors, and automatically compensating for variables in signal and circuit parameters.

The measurement of gas concentrations by using infrared detectors is typically accomplished by application of Beer's Law, which can predict the amount of absorption of an infrared signal wavelength passing through a region of concentration of a particular target gas, according to the formula:

$$I=I_o \, e^{-\gamma l c}; \text{ where}$$

I is the signal after absorption;
$I_o$ is the signal before absorption;
$\gamma$ is the absorption coefficient of the gas;
l is the path length through the gas; and
c is the gas concentration.

In designing such a measurement system, it is common to use two infrared channels, each developing an infrared signal at a different frequency (wavelength), where one wavelength is known to be particularly sensitive to absorption in the chosen target gas, and the other wavelength is known not to be particularly sensitive to absorption in the chosen target gas. Therefore, the concentration of the target gas can be measured by taking the ratio of the signal strength of the non-sensitive wavelength (the reference channel) to the signal strength of the sensitive wavelength (the analytical channel).

The two infrared channels can be developed using a single infrared source positioned at a fixed distance from two wavelength bandpass filters which are sensitive to various wavelengths as described above, and permitting the target gas to fill the space and distance between the source and the two filters. One channel is chosen so as to pass frequencies in the infrared band, but the bandpass filters are centered on a wavelength known to be highly absorbed in the target gas; this channel is known as the "analytical" channel. The other channel is chosen so as to pass frequencies in the infrared band, close to the bandpass frequencies of the first channel, with the bandpass filters centered on a wavelength which is not highly absorbed in the target gas; this channel is known as the "reference" channel. For example, if measuring a hydrocarbon gas such as methane, the reference channel sensitivity would be set to a wavelength of 3.9 microns, and the analytical channel sensitivity would be set to a wavelength of 3.4 microns. Most of the environmental factors which may be present will affect both the analytical and the reference channel in a similar manner, but the presence of a target gas affects primarily the analytical channel. A quotient, formed by dividing the reference signal value by the analytical signal value, will only change when a target gas is present in the optical path of the infrared channels; the amount of quotient change can be used to calculate the target gas concentration using Beer's Law.

There are a number of factors which can degrade accuracy in the foregoing scheme. The infrared sensors are necessarily analog devices, although the time-varying analog voltage signals they produce are frequently converted to digital values through the use of analog-to-digital converters (A/D converters) to obtain greater precision. If the analog voltage signals become too large they can exceed the bounds of the A/D converter; if the analog voltage signals become too small they produce poor resolution of the digital converted value, and both of these factors can lead to a reduction in accuracy of the measured values. Another cause of reduced accuracy is component tolerance variations, particularly in the photo elements, which make it difficult to control analog voltage levels from unit to unit; this can be addressed by providing adjustable potentiometers in the circuits, for making tolerance adjustments during the manufacturing process. Another cause of reduced accuracy, after units are placed into operation, is that the optical components of a system can become coated with dust or other substances which attenuate the light passing through, reducing the analog voltage signal levels produced by the optical detectors; similarly, the output light intensity level typically lowers as a light source ages, which also reduces the analog voltage signal level. These problems can been addressed by frequently cleaning the optical path components and using manual potentiometer adjustments as the equipment ages.

Another cause of inaccuracy is the variation in absorption coefficients of different gases, which causes the absorption response curve to vary from gas to gas, and also from one gas concentration level to another. This problem can be addressed by choosing specific, selectable, families of response curves for specific gases, and different analog voltage gain values for the electronic circuits used to detect the gas concentrations. Another cause of inaccuracy is temperature variations in the measurement environment, which can cause changes in circuit performance in the measurement system.

Most of the foregoing problems are more or less continuously present, and frequent readjustments of circuit parameters and frequent cleaning are inadequate for ensuring a smooth, continuously accurate measurement result. It is therefore a principal object of the present invention to provide a stable, continuously accurate measurement system for monitoring gas concentrations in a particular environment. Specifically, it is an object of the present invention to provide a circuit for automatically adjusting analog voltage signal levels to keep the permissible signal range constant, ie., to maintain the maximum permissible signal at a constant voltage span relative to the "zero" signal level; it is also an object of the invention to provide circuit compensation for variations or drift in the "zero" or reference voltage signal level, and for circuit gain variations caused by any of the aforementioned effects. The foregoing objects advantageously provide a circuit for automatically controlling variables related to measuring analog voltage signals from infrared gas detection devices, by providing a constant zero point for analog voltage signals, a constant voltage value representing the full-scale point for the same signals, an adjustable gain circuit to compensate for changes in overall circuit gain, and an absorption coefficient response curve for any known gas, which is accurate to a first order approximation.

SUMMARY OF THE INVENTION

A control and measurement circuit responsive to analog voltage signals produced by infrared sensors in a gaseous environment, including a computer processor connected to receive signals from the infrared sensors after the circuit's zero reference voltage has been calibrated by a BALANCE circuit, the circuit's gain has been adjusted by an AGC circuit and the circuit's voltage range has been set by a SPAN circuit, wherein each of these circuits has a digitally-controllable potentiometer as an input impedance, wherein each potentiometer is adjustable by binary voltage feedback signals generated by a computer processor. As a result, the analog voltages present within the circuit during the calibration process are converted to digital values which are used by software within the computer processor to generate digital feedback signals to the respective BALANCE, AGC, and SPAN circuits to adjust the respective circuit's analog voltage response characteristics.

The computer processor receives the analog voltage signals generated by the infrared sensors and converts them to digital values for internally comparing the digital values to a prestored Beer's Law curve for the particular gas being measured, for providing a measurement of the concentration of the gas being measured.

BRIEF DESCRIPTION OF THE DRAWINGS

The foregoing objects of the invention will become apparent from the following description of a preferred embodiment of the invention, and with reference to the appended drawings, in which.

DESCRIPTION OF THE PREFERRED EMBODIMENT

Figure 1:
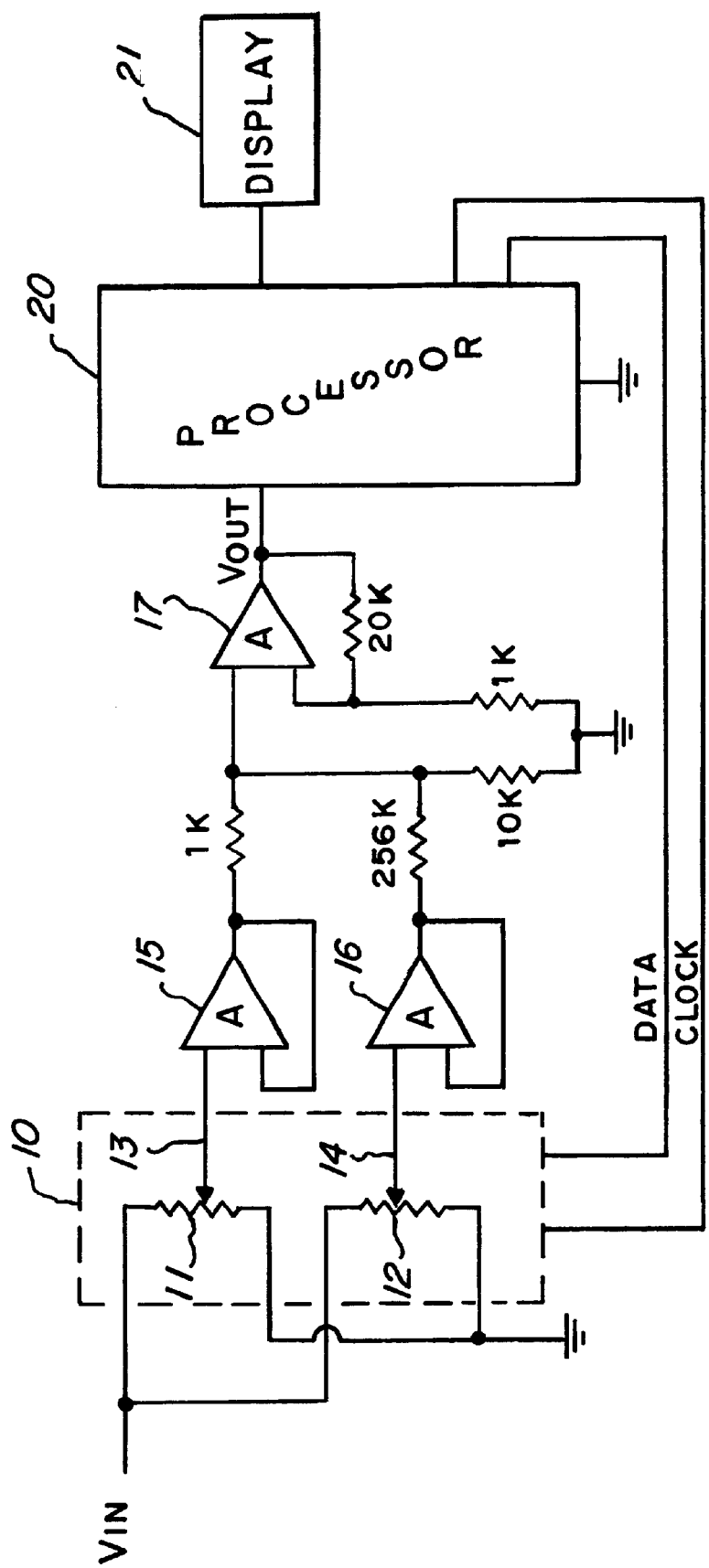
FIG. 1 shows a symbolic block diagram of amplifier circuits having a digitally-adjustable potentiometer input circuit, wherein the circuit output is connected to a digital processor, which is part of a closed loop feedback circuit.

Referring first to FIG. 1, there is shown a group of three amplifier circuits having a processor-addressable dual digital potentiometer 10 input circuit and a computer processor 20 output circuit, illustrating the essential circuit connections which form the heart of the present invention. The processor 20 output circuit is shown in FIG. 1 as a display 21, but this is representative of any type of computer output circuit or device which is known in the art. The addressable dual digital potentiometer 10 is a commercially available component, as for example, a type DS1803 manufactured by Dallas Semiconductor Corporation. Each potentiometer 11, 12 represented within the box 10 consists of a resistor array having 256 selectable positions, formed by a series-connected plurality of semiconductor MOSFET devices, each of which are switchable "on" or "off" by a binary voltage signal, and an 8-bit register (not shown) to receive the binary voltage signals, and thereby to effectively set the "wiper" 13, 14 position to any of the 256 positions, depending on the digital value of the binary voltage combination loaded into the register. The potentiometers 11, 12 are connected together at their respective ends, and the top end connection is connected to an analog input voltage signal $V_{IN}$ and the bottom end connection is connected to a voltage ground.

The device is addressable and controlled by a two-wire serial interface over the lines "data" and "clock," which are connected to the computer processor 20 serial output port. The computer processor 20 provides data for loading into the potentiometer registers, under control of a clock signal also provided by the processor 20.

Each potentiometer wiper 13, 14 is connected to a separate amplifier 15, 16 having essentially identical transfer characteristics. The amplifier is a non-inverting, fixed gain operational amplifier. The output signal from amplifier 15 is connected to an amplifier 17 input via a 1000-ohm (1K) resistor, and the output signal from amplifier 16 is connected to the same amplifier 17 input via a 256 K resistor, thereby providing an additive input signal, where the two input signals are summed in the ratio of 256/1 to the amplifier 17 input from the respective amplifiers 15, 16. This provides an effective "high byte" and "low byte" contribution to the output voltage from amplifier 17, where the output voltage is directly proportional to the input voltage, with a signal resolution of one part in $2^{16}$. The output signal from amplifier 17, $V_{OUT}$, is applied to an analog-to-digital input terminal of computer processor 20, and therefore produces a digital value to the computer processor which is representative of the analog input voltage $V_{IN}$, to a resolution of one part in 65,536 ($2^{16}$).

Figure 2:
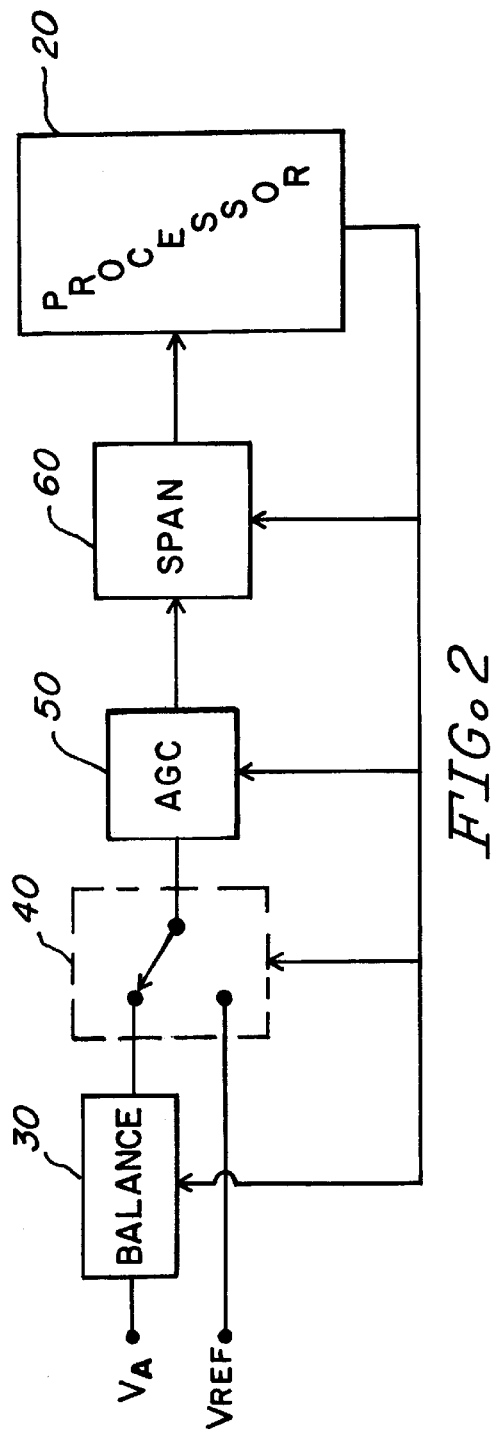
FIG. 2 shows a block diagram of the invention.

FIG. 2 shows a block diagram of the present invention, illustrating the major circuit functions, BALANCE, AGC, and SPAN, which are used to achieve the control desired herein, all in conjunction with the computer processor 20. Each of the circuit functions contains circuit components as shown in FIG. 1, and each circuit function is operated under the control of the processor 20. The BALANCE circuit 30 has an input connected to receive the analog voltage signal $V_A$ from an infrared sensor, and an output connected to a switch terminal of switch 40. Another switch terminal of switch 40 is connected to a source of reference voltage $V_{REF}$, which could come from a second infrared sensor, and the third terminal of switch 40 is connected to an input of AGC circuit 50. The output of AGC circuit 50 is connected to the input of SPAN circuit 60, and the output of SPAN circuit 60 is connected to an A/D input connection to processor 20. If two infrared sensors are used to connect to the switch 40, they are typically sensors which are responsive to different wavelengths of light. The $V_A$ signal is from a sensor monitoring the environment where a concentration of the gas desired for detection might be found, and the $V_{REF}$ signal is from a sensor monitoring the same environment but which is non-responsive to the gas desired for detection.

Figure 3:
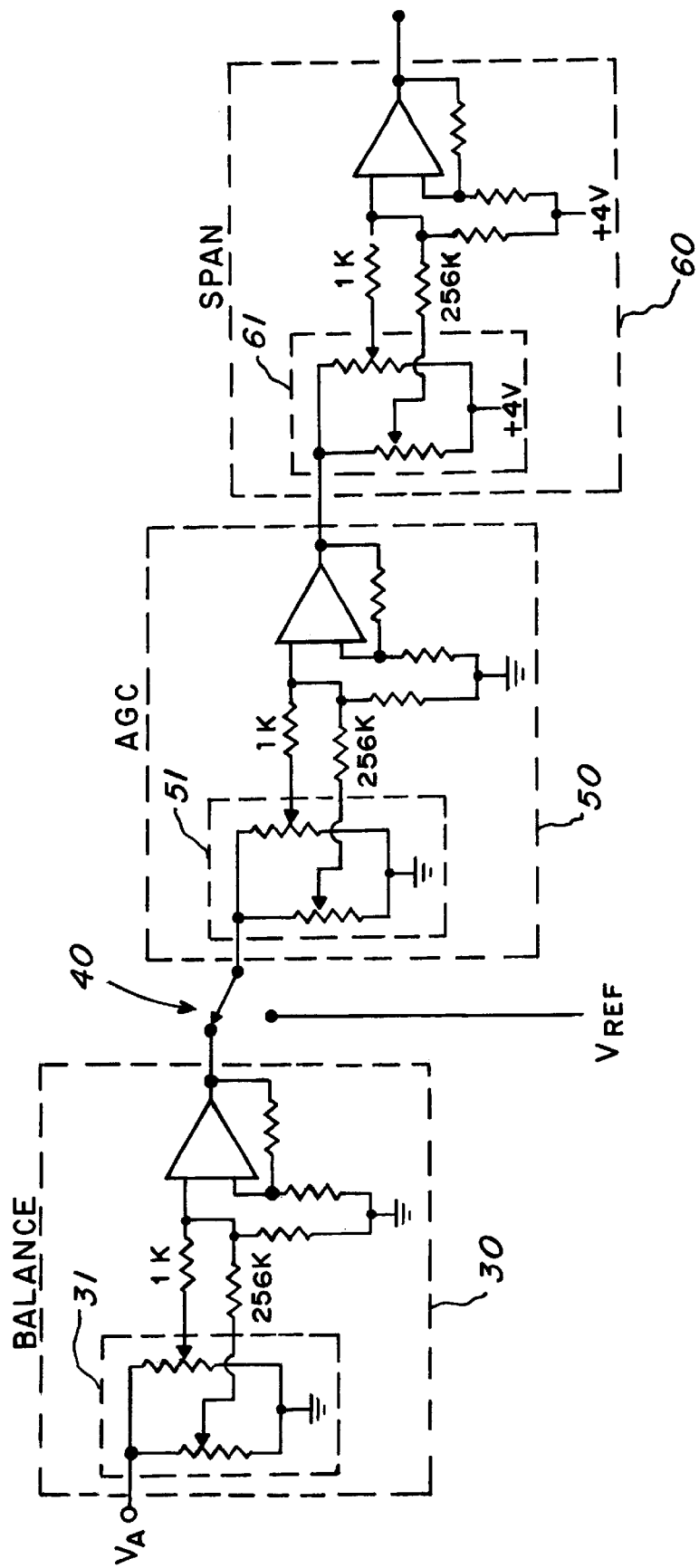
FIG. 3 shows a circuit diagram of the several amplifier circuits of the invention, each connected to an addressable dual digital potentiometer.

FIG. 3 shows a simplified circuit diagram of the several circuits described above; it should be apparent that the circuit connections of each of the circuits is virtually identical to the other circuits, with the exception that the SPAN circuit is referenced to a +4 VOLT power supply rather than to circuit ground as are the AGC and BALANCE circuits. Each circuit has an addressable dual digital potentiometer associated with an amplifier as described earlier; namely, the BALANCE circuit 30 has a dual digital potentiometer 31 associated therewith, the AGC circuit 50 has a dual digital potentiometer 51 associated therewith, and the SPAN circuit 60 has a dual digital potentiometer 61 associated therewith. In each case, the computer processor 20 is connected, via a "DATA" and "CLOCK" signal line, to provide the register settings for the respective digital potentiometers.

In operation, the circuits are first manipulated through a calibration procedure to select the initial settings for the AGC, BALANCE and SPAN potentiometers. Because of the particular circuits selected for the preferred embodiment, the "zero" voltage reference is selected to be +4.0 volts, and the maximum gas concentration voltage is selected to be +0.5 volts. Since the infrared detector converts light intensity to voltage, this voltage selection translates into a Beer's Law equation of:

$$V = V_o e^{-\gamma lc}$$

$V_o$=+4.0 volts; therefore, $$V = 4.0\, e^{-\gamma lc}$$

Since the maximum, or full scale value of the Beer's Law calculation is +0.5 volts, we can calculate the value of the exponent at the maximum gas concentration level (cmax):

$0.5 = 4.0 e^{-\gamma lcmax}$; taking the log of each side: $-\text{Ln}\,(0.5/4.0) = \gamma lcmax = 2.08$ The foregoing calculations set the parameters for the Beer's Law equation in the context of the actual circuit parameters used for this invention; namely, a voltage indication of 4.0 volts when zero gas concentration exists in the sensor environment, and a voltage indication of 0.5 volts when a maximum gas concentration exists in the sensor environment. For all other concentrations of gas the following Beer's Law formula can be solved for any measured voltage "V":

$$V = 4.0\, e^{-\gamma lc}$$

The calibration procedure can proceed according to the following steps. First, the processor selects the switch 40 and sets switch 40 to select the reference channel, which is the $V_{REF}$ position, and which corresponds to a zero gas concentration reference, and the AGC potentiometer is selected by the processor. The processor sends binary digital feedback signals to the input registers of the AGC digital potentiometer circuit to obtain an input voltage to the computer processor of 4.0 volts. Thus, the gain is set by the processor to reflect the zero gas concentration value to the processor.

Next, the processor selects the switch 40 and sets switch 40 to select the analytical channel, which is the $V_A$ position, under conditions of zero gas concentration in the sensor environment. The processor sends binary digital feedback signals to the input registers of the BALANCE potentiometer circuit to obtain an input voltage to the computer processor of 4.0 volts. This provides a sensor signal value to the processor corresponding to the zero gas concentration value set in the previous step.

Next, a known gas of known concentration is injected into the infrared detector environment; the selected gas concentration is preferably ½ the maximum obtainable concentration level, or ½ cmax as derived above. This represents a gas concentration "c" equal to "cmax/2". and the Beer's equation becomes:

$V$(½ gas concentration) $= 4e^{-1.04} = 1.414$ volts

Figure 4:
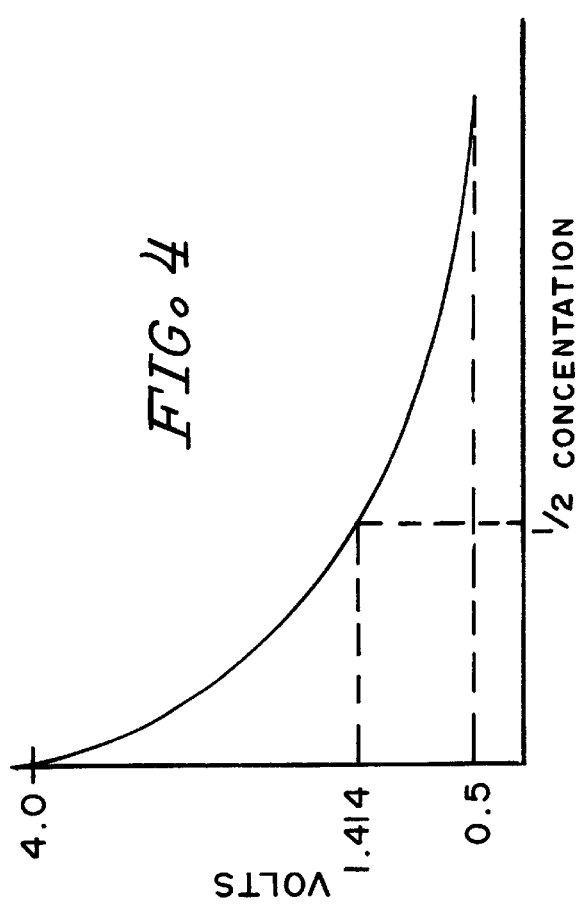
FIG. 4 shows a typical gas concentration curve for a gas according to Beer's Law.

The processor sends binary digital feedback signals to the SPAN potentiometer circuit to obtain an input voltage to the computer processor of 1.414 volts, which is the voltage associated with the target gas at ½ concentration (see FIG. 4).

Having determined the ½-concentration voltage, any other voltage ($V_M$) measured by the processor can be used to calculate any unknown gas concentration ($C_u$) using Beer's Law. The processor constructs the Beer's Law curve of FIG. 4 and prestores this curve in memory, either in the form of a table look-up or in any other convenient form useful to the processor, because three points along the exponential curve are known from the foregoing calibration steps, and therefore all other points along the curve can be plotted or calculated. Any subsequent voltage received by the processor can be applied to the known exponential curve, and the gas concentration corresponding to that voltage value can be determined from the prestored table or curve.

Once the device is calibrated it can then be operated in real time, with unknown concentrations of target gas passing into the infrared sensor device. In real time operation, the switch 40 is switched four times per second to regularly measure the reference voltage at the computer, and to change the binary digital feedback value to the AGC potentiometer if necessary to return the measured value to +4.0 VOLTS. This AGC potentiometer change is effective for adjusting the reference sensor voltage value received by the processor, which also adjusts the analytical sensor voltage value, on the theory that whatever outside influence caused the drift in the "zero" voltage value would also cause an identical drift in the analytical sensor value.

During the time the switch is connected to the sensor via the analytical channel, the actual gas concentration being measured is presented to the computer processor 20 input in the form of a voltage ranging between the zero concentration level (+4.0 VOLTS) and the full scale concentration level (+0.5 VOLTS); the actual measured voltage is applied to the curve of FIG. 4, or to a curve-fitting process residing in computer software, to derive the relative gas concentration being measured. The BALANCE potentiometer circuit and the SPAN potentiometer circuit are not subsequently readjusted, unless a new calibration procedure is necessary. This operating procedure provides a sensor reading to the processor four times a second, and also provides a gain adjustment, if necessary, four times a second.

The essential advantage of the invention is that the analog signals over the zero to full scale range are always identical regardless of the type of gas being measured, the range of concentrations of the gas, the amount of signal drift which occurs, and the signal degradation which may occur. It enables determination of gas concentrations using Beer's Law a matter of trivial complexity, involving only a single response curve, where the analog signals can't exceed the boundaries set for the device and the A/D resolution is constant.

The present invention may be embodied in other forms without departing from the spirit or essential attributes thereof; and it is, therefore, desired that the preferred embodiment be considered in all respects as illustrative and not restrictive, reference being made to the appended claims rather than to the foregoing description to indicate the invention scope.

What is claimed is:

1. An apparatus for measuring the concentration of a target gas using an infrared detector wherein the detector has a first output voltage representative of a first infrared wavelength absorbed by the target gas concentration, and has a second reference output voltage representative of a second infrared wavelength not absorbed by the target gas concentration, comprising:
   a) a BALANCE circuit connected to receive the first output voltage, said BALANCE circuit having a digitally controlled input potentiometer circuit having an addressable dual digital potentiometer which is separately addressable over control signal lines, whereby the input potentiometer circuit is initially set to provide a BALANCE circuit output voltage indicative of zero target gas concentration;
   b) a two-position switch connected to said second reference output voltage and to said BALANCE circuit output, said switch being selectable to connect either of said second reference output voltage or said BALANCE circuit output to a switch output terminal;

c) an AGC circuit connected to said switch output terminal, said AGC circuit having a digitally controlled input potentiometer circuit, said input potentiometer circuit having an addressable dual digital potentiometer which is separately addressable over control signal lines, being periodically adjusted to provide an AGC output circuit voltage equal to said second reference output voltage;

d) a SPAN circuit connected to said AGC output voltage, said SPAN circuit having a digitally controlled input potentiometer circuit comprising an input circuit having an addressable dual digital potentiometer which is separately addressable over control signal lines, and having a SPAN output terminal and said digitally controlled input potentiometer circuit being adjustable to provide a SPAN output voltage at said SPAN output terminal; and e) a computer processor connected to receive said SPAN output voltage, and having means for converting said SPAN output voltage to a digital value, said computer processor further having said control signal lines connected to said AGC circuit digitally controlled input potentiometer circuit, said SPAN circuit digitally controlled input potentiometer circuit, and said BALANCE circuit digitally controlled input potentiometer circuit, said computer processor further having means for generating control signals over said control lines in response to said SPAN output voltage, said control signals further control in said switch position, said AGC circuit output voltage, said BALANCE circuit output voltage, and said SPAN output voltage.

2. The apparatus of claim 1, wherein each of said dual digital potentiometers further comprises a resistance ladder and means for selecting a resistance on said ladder by addressable values over said control lines.

3. The apparatus of claim 2, wherein each of said resistance ladders further comprise at least 256 separately selectable resistance values.

4. An apparatus for measuring gas concentration of a target gas in an infrared detector by comparison to a reference gas in said infrared detector, by measuring relative infrared signal absorption by said target gas in comparison to signal absorption by said reference gas, comprising:

a) a first circuit connected to receive a first signal from said detector representative of said target gas relative signal absorption, said first circuit having a digitally controlled potentiometer input circuit which is adjustable by a computer processor, and having a first circuit output terminal;

b) a switch connected to receive a second signal from said detector representative of said reference gas signal absorption, said switch also connected to said first circuit output terminal, and said switch having a switchable output terminal and being controllable by a computer processor;

c) a second circuit connected to receive the signal from said switch switchable output terminal, said second circuit having a digitally controlled potentiometer input circuit which is adjustable by a computer processor, and having a second circuit output terminal;

d) a third circuit connected to receive the signal from said second circuit output terminal, said third circuit having a digitally controlled potentiometer input circuit which is adjustable by a computer processor, and having a third circuit output terminal;

e) a computer processor connected to said first, second, and third circuits' respective digitally controlled potentiometer input circuits, and connected to said controllable switch, and connected to said third circuit output terminal, whereby to control the respective circuit's output signals in response to signals received from said third circuit output terminal.

5. The apparatus of claim 4, wherein each of said digitally controlled potentiometer input circuits respectively comprise a resistor ladder circuit having a plurality of selectable resistance values, and whereby the selection of said selectable resistance values is made by connections to said computer processor and programmable computer processor signals.

6. The apparatus of claim 4, wherein each of said digitally controlled potentiometer input circuits respectively comprise two resistor ladder circuits connected in parallel to receive an input signal, each ladder circuit having a plurality of selectable resistance values and each ladder circuit separately connected to an amplifier circuit, and whereby the selection of said selectable resistance values is made by connections to said computer processor and programmable computer processor signals.

7. The apparatus of claim 6, wherein said each plurality of selectable resistance values further comprises eight, and wherein said respective ladder circuits' connection to an amplifier circuit is through respective series resistance connections in the ratio of 256/1.

8. The apparatus of claim 7, wherein each said amplifier circuit has an output terminal, and wherein both of said amplifier circuits' output terminals are connected to an input terminal of a further amplifier.

9. An apparatus for measuring gas concentration using an infrared detector, wherein the detector output voltage is representative of gas concentration, and using a reference voltage source, comprising:

a) a first amplifier circuit having a first resistance input connected to receive said detector output voltage, wherein said first resistance input further comprises a plurality of series-connected resistances and a first register for receiving a digital binary value, and means for selecting combinations of said series-connected resistances according to the digital binary value in said first register;

b) a switch connected to said first amplifier circuit and to said source of reference voltage source, and having a switchable output;

c) a second amplifier circuit having a second resistance input connected to said switchable output, wherein said second resistance input further comprises a plurality of series-connected resistances and a second register for receiving a digital binary value, and means for selecting combinations of said series-connected resistances according to the digital binary value in said second register;

d) a third amplifier circuit having a third resistance input connected to said second amplifier circuit, wherein said third resistance input further comprises a plurality of series-connected resistances and a third register for receiving a digital binary value, and means for selecting combinations of said series-connected resistances according to the digital binary value in said third register;

e) a computer processor connected to said third amplifier circuit, said computer processor having means for generating binary digital values for each of said first, second and third registers; and f) feedback means connected between said computer processor and each of said first, second and third registers, for transferring binary digital values from said computer processor to each of said first, second and third registers.

10. The apparatus of claim 9, further comprising feedback means from said computer processor to said switch, for selectively actuating said switch from one position to another.

11. The apparatus of claim 10, wherein each of said first, second and third series-connected resistances respectively further comprises a plurality sufficient to provide 256 different combinations of resistances.

12. The apparatus of claim 10, wherein each of said first, second and third series-connected resistances respectively further comprises a first plurality of series-connected resistances and a second plurality of series-connected resistances, said second plurality being connected in parallel to said first plurality.

* * * * *